(12) United States Patent
Guida et al.

(10) Patent No.: US 6,797,477 B2
(45) Date of Patent: Sep. 28, 2004

(54) GENETIC TYPING OF THE HUMAN CYTOCHROME P450 2A6 GENE AND RELATED METHODS

(75) Inventors: Marco Guida, San Diego, CA (US); Jeff Hall, Carlsbad, CA (US)

(73) Assignee: Genaissance Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 10/232,634

(22) Filed: Aug. 30, 2002

(65) Prior Publication Data

US 2003/0105314 A1 Jun. 5, 2003

Related U.S. Application Data

(62) Division of application No. 09/586,376, filed on Jun. 2, 2000, now Pat. No. 6,492,115.

(51) Int. Cl.[7] .............................. C12Q 1/68; C12Q 1/44; C12P 19/34; C07H 21/04

(52) U.S. Cl. ............................ 435/6; 435/19; 435/91.2; 536/23.2; 536/23.5; 536/24.31

(58) Field of Search .............................. 435/6, 19, 91.2; 536/23.2, 23.5, 24.31

(56) References Cited

U.S. PATENT DOCUMENTS 5,891,633 A * 4/1999 Gonzalez et al. ............... 435/6
5,974,164 A 10/1999 Chee ........................... 382/129

FOREIGN PATENT DOCUMENTS

| WO | WO 95/34679 | 12/1995 |
| WO | WO 98/03171 | 1/1998 |
| WO | WO 99/27919 | 6/1999 |

OTHER PUBLICATIONS

Fernandez–Salguero et al.; "A genetic polymorphism in coumarin 7–hydroxylation: sequence of the hunam CYP2A genes and Identification of variant CYP2A6 alleles"; *Am J Hum Genet*; 1995; Sep;57(3); abstract only.

Inoue et al.; "CYP2A6 genetic polymorphisms and liver microsomal coumarin and nicotine oxidation activities in Japanese and Caucasians"; *Arch Toxicol*; 2000; *73 (10–11)*; abstract only.

Kitagawa et al.; "The Significance of the Homozygous CYP2A6 Deletion on Nicotine Metabolism: A New Genotyping Method of CYP2A6 Using a Single PCR–RFLP"; *Biochemical and Biophysical Research Communications*; 1999; *262*; pp. 146–151.

London et al.; "Genetic variation of CYP2A6, smoking, and risk of cancer"; *Lancet*; 1999; *353*; pps. 898–899.

Nakajima, T. et al.; "Characterization of the human cytochrome P450 isozymes responsible for styrene metabolism"; *IARC Sci Publ*; 1993; *127*; abstract only.

Oscarson et al.; "Characterisation and PCR–based detection of a CYP2A6 gene deletion found at a high frequency in a Chinese population"; *FEBS Letters*; 1999; *448*; pp. 105–110.

Oscarson et al.; "Identification and characterisation of novel polymorphisms in the CYP2A locus: Implications for nicotine metabolism"; *FEBS Letters*; 1999; *460*; pp. 321–327.

Oscarson et al., "Genotyping of human cytochrome P450 2A6 (CYP2A6) a nicotine C–oxidase"; *FEBS Letters;* 1998; *438*; pp. 201–205.

Pianezza et al.; "Nicotine metabolism defect reduces smoking"; *Nature*; 1998; *393*; p. 750.

(List continued on next page.)

Primary Examiner—Diana B. Johannsen
(74) Attorney, Agent, or Firm—Sandra L. Shaner

(57) ABSTRACT

Disclosed are novel polymorphisms in the human cytochrome P450 2A6 gene and the use of those polymorphisms as predictive sequences for altered metabolism or occurrence of disease.

10 Claims, 1 Drawing Sheet-

OTHER PUBLICATIONS

Raunio et al.; "Metabolic Polymorphisms and Susceptibility to Cancer"; *IARC Scientific Publications*; 1999; *148*; pp. 197–207.

Fernandez–Salguero et al., 1995, *Am. J. Hum. Genet.*, 57:651–660.

Nunoya et al., 1990, *J. Pharmacol. Exp. Ther.*, 289(1):437–442.

Nunoya et al., 1988, *Pharmacogenetics*, 8:239–249.

Yamano et al., 1990, *Biochem.*, 29:1322–1329.

Miles, et al., 1989, *Nucleic Acids Res.*, 17(8):2907–2917.

Celniker, et al., GenEmbl Accession No. AC005635 (Dec. 1998).

* cited by examiner-

GENETIC TYPING OF THE HUMAN CYTOCHROME P450 2A6 GENE AND RELATED METHODS

CROSS REFERENCE TO RELATED APPLICATION

The present application is a divisional of U.S. patent application Ser. No. 09/586,376, filed Jun. 2, 2000, now U.S. Pat. No. 6,492,115, entitled "GENETIC TYPING OF THE HUMAN CYTOCHROME P450 2A6 GENE AND RELATED MATERIALS AND METHODS," which is incorporated herein by this reference.

FIELD OF THE INVENTION

The present invention relates to the identification of various polymorphisms in the cytochrome P450 2A6 gene and methods and reagents for genotyping and phenotyping individuals using such polymorphisms.

BACKGROUND OF THE INVENTION

The mammalian liver contains enzymes that convert various chemical compositions to products which can more easily be eliminated from the body. One enzyme system which plays a major role in determining the rate of elimination of these drugs is cytochrome P450. The cytochrome P450's are among the major constituent proteins of the liver mixed function monooxygenases. They play a central role in the metabolism of steroids, the detoxification of drugs and xenobiotics, and the activation of procarcinogens. Without cytochrome P450 and related enzymes, naturally occurring and man-made foreign chemicals would accumulate in the body. Additionally, the biological effects of some chemicals are due solely to metabolites generated by cytochrome P450 and/or related enzymes. Metabolism by cytochrome P450 enzymes is often the rate-limiting step in pharmaceutical elimination. For example, most phase I metabolism of drugs and environmental pollutants is performed by cytochrome P450 enzymes. In this process, one or more water-soluble groups (such as hydroxyl) are introduced into the fat-soluble parent molecule, thereby rendering it vulnerable to attack by the phase II conjugating enzymes. The increased water-solubility of phase I and especially phase II products permits ready excretion. Consequently, factors that lessen the activity of cytochrome P450 enzymes usually prolong the effects of pharmaceuticals, whereas factors that increase cytochrome P450 activity have the opposite effect.

The phenobarbital-inducible P450 gene, CYP2A6 or CYP4502A6, is a member of a multigene family located on by human chromosome 19. Induction by phenobarbital is mediated almost entirely at the level of transcription. P450 enzymes, as well as other so called "drug-metabolizing" enzymes, play an important role in maintaining the steady-state levels of endogenous ligands involved in ligand-modulated transcription of genes effecting homeostasis, growth, differentiation, and neuroendocrine functions.

Genetic polymorphisms of cytochrome P450 enzymes result in subpopulations of individuals that are distinct in their ability to perform particular drug biotransformation reactions. These phenotypic distinctions have important implications for selection of drugs. For example, a drug that is safe when administered to the majority of humans may cause intolerable side-effects in an individual suffering from a defect in a cytochrome P450 enzyme required for detoxification of the drug. Alternatively, a drug that is effective in most humans may be ineffective in a particular subpopulation because of the lack of a particular cytochrome P450 enzyme required for conversion of the drug to a metabolically active form. Accordingly, it is important for both drug development and clinical use to screen drugs to determine which cytochrome P450 enzymes are required for activation and/or detoxification of the drug.

It is also important to identify those individuals who are deficient in a particular P450 enzyme. This type of information has been used to advantage in the past for developing genetic assays that predict phenotype and thus predict an individual's ability to metabolize a given drug. Information such as this would be of particular value in determining the likely side effects and therapeutic failures of various drugs and routine phenotyping could be recommended for certain categories of patients.

Wood and Conney, Science, 1974, vol. 185, pages 612–614, found that basal and phenobarbital-induced rates of hepatic metabolism of coumarin to 7-hydroxycoumarin were markedly higher in DBA-2J mice than in other strains and that intermediate activities in hybrids indicated codominant inheritance. They suggested that there could be similar variability in man. Kratz, Europ. J. Clin. Pharm., 1976, vol. 10, pages 133–137, studied coumarin 7-hydroxylase activity in human liver obtained by needle biopsy. A 4-fold range of enzymatic activity was observed and Kratz suggested that the difference was due to genetic differences between sample donors. Kratz excluded individuals taking drugs that might induce enzyme activity from the study. Yamano et al., Biochemistry, 1990, vol. 29, pages 1322–1329, reported a variant allele of the CYP2A6 gene termed *2 that had a single nucleotide substitution that resulted in an amino acid substitution of a histidine for a leucine at position 160. The variant allele was found to encode an unstable and catalytically inactive enzyme. Fernandez-Salguero et al., Am. J. Hum. Genet., 1995, vol. 57, pages 651–660, reported the genomic sequence for the CYP2A6, CYP2A7, and CYP2A 13 genes, in addition to 2 pseudogenes truncated after exon 5, located on 19q13.2. They also identified three different CYP2A6 alleles: the functional CYP2A6 allele, referred to as *1; the variant-1 allele that had a single base mutation of a T to an A resulting in a substitution of a histidine for a leucine in exon 3, referred to as *2; and the variant-2 allele which was formed by gene conversion between the wildtype CYP2A6 and CYP2A7 genes in exons 3, 6, and 8, referred to as *3.

Four different deletion mutants resulting in an absence of enzyme activity have been described by prior investigators. Oscarson et al., FEBS Lett., 1999, vol. 448, pages 105–110), described the structure of a novel CYP2A locus, referred to as *4A, in which the entire CYP2A6 gene had been deleted thereby disrupting CYP2A6-dependent metabolism. They proposed that this allele was generated by an unequal crossover event between the 3-prime flanking region of the CYP2A6 and CYP2A7 genes. A "D-type" deletion mutant lacking the CYP2A6 gene region from intron 5 to exon 9, referred to as *4B, was described by Nonoya et al., Pharmacogenetics, 1998, vol.8, pages 239–249. An "E-type" mutant referred to as *4C was also identified by Nonoya et al., J. Pharmacol Exp Ther., 1999, vol.289, pages 437–442 in which exons 1, 8, and 9 of CYP2A6 gene were deleted. Oscarson et al., FEBS Lett., 1999, vol. 460, pages 321–327, identified a fourth type of deletion mutant referred to as *4D that they suggested resulted from unequal crossover event with a junction at either intron 8 or exon 9. In addition to characterizing the new deletion mutant CYP2A6*4D, Oscarson et al. also reported a new variant referred to as *5 that was a single nucleotide change of G to T at position 1436, resulting in a substitution of a valine for a glycine at codon 479. This variant allele resulted in a poor metabolizer phenotype. In addition, they found a new wild type variant referred to as *1B that resulted from a gene conversion in the 3' flanking region of the CYP2A6 gene.

It has been established in the art that nicotine is inactivated by c-oxidation to cotinine. Tyndale, PCT Publication No. WO 98/03171, published Jan. 29, 1998, disclosed that inhibitors of the enzyme encoded by the CYP2A6 gene cause a decrease in nicotine metabolism. It has been suggested in the art that the enzyme encoded by the CYP2A6 gene may affect smoking patterns by mediating the metabolism of nicotine (Vineis et al., in Metabolic Polymorphisms and Susceptibility to Cancer, IARC Scientific Publication No. 148, 1999). Pianezza et al., Nature, 1998, vol. 393, page 750, disclosed that smokers carrying two null CYP2A6 alleles consumed fewer cigarettes. Oscarson et al., FEBS Lett., 1998, vol. 438, pages 201–205, however, indicated that Pianezza et al. used an erroneous method to measure the association of the genotype to the phenotype and therefore additional studies need to be performed to correctly determine the true phenotype of individuals that are genetically CYP2A6 defective. London et al., Lancet, 1999, vol. 353, pages 898–899, also disclosed that polymorphism in the CYP2A6 gene has little influence on the propensity to smoke cigarettes. Seller and Tyndale, PCT Publication No. WO 99/27919, published Jun. 10, 1999, disclosed that the presence of the *2 and *3 mutant alleles of CYP2A6 are related to whether an individual becomes a smoker or if already a smoker, then the number of cigarettes that person smokes. Seller and Tyndale conclude that the CYP2A6 genotype directly influences the risk for tobacco dependence. Genotyping methods using variants of the CYP2A6 gene have been suggested by prior investigators (e.g., Kitagawa et al., Biochem Biophyis Res Comm, 1999, vol. 262, pages 146–151).

None of the previous investigators, however, have identified the polymorphisms of the present invention and their associated any genetic variation with the susceptibility or occurrence of inflammation, asthma or habitual smoking.

There still remains a need in the art to identify polymorphisms in the CYP2A6 gene that have predictive value for altered metabolism or occurrence of disease.

SUMMARY OF THE INVENTION

The present invention relates to novel polymorphisms located in the human CYP2A6 gene and the use of those polymorphisms as predictive sequences for altered metabolism or occurrence of disease. According to the present invention there are provided CYP2A6 polymorphic nucleic acid sequences and methods to use such nucleic acid sequences, in particular for diagnostic purposes to identify individuals having a polymorphic genotype.

One embodiment of the present invention includes an isolated nucleic acid molecule having a nucleic acid sequence selected from the group consisting of SEQ ID NO:10, SEQ ID NO:12, SEQ ID NO:14, SEQ ID NO:16, SEQ ID NO:18, and SEQ ID NO:20 and nucleic acid sequences that are fully complementary thereto. Another embodiment of the present invention includes an isolated nucleic acid molecule that comprises at least one base variation from that of a known human P450 sequence, wherein the nucleic acid molecule is selected from the group consisting of:(a) a nucleic acid molecule that comprises a T for a C at position 202 of SEQ ID NO:21 and at least 20 other bases of SEQ ID NO:21 contiguously appurtenant to said position; (b) a nucleic acid molecule which comprises a C for a T at position 369 of SEQ ID NO:21 and at least 20 other bases of SEQ ID NO:21 contiguously appurtenant to said position; (c) a nucleic acid molecule which comprises an A for a G at position 394 of SEQ ID NO:21 and at least 20 other bases of SEQ ID NO:21 contiguously appurtenant to said position; (d) a nucleic acid molecule which comprises an A for a C at position 413 of SEQ ID NO:21 and at least 20 other bases of SEQ ID NO:21 contiguously appurtenant to said position; (e) a nucleic acid molecule which comprises a G for a T at position 743 of SEQ ID NO:21 and at least 20 other bases of SEQ ID NO:21 contiguously appurtenant to said position; (f) a nucleic acid molecule which comprises an A for a G at position 841 of SEQ ID NO:21 and at least 20 other bases of SEQ ID NO:21 contiguously appurtenant to said position; and (g) a nucleic acid molecule which is fully complementary to a nucleic acid molecule of (a)–(f).

Further embodiments of the invention include various methods for identifying polymorphisms. One such method is a method for identifying a polymorphism in a nucleic acid molecule of an individual which includes determining whether a nucleic acid sequence selected from SEQ ID NO:10, SEQ ID NO:12, SEQ ID NO:14, SEQ ID NO:16, SEQ ID NO:18, and SEQ ID NO:20 or a nucleic acid sequence that is fully complementary thereto is present in the nucleic acid molecule. Two other such methods include a method for evaluating an individual's risk of developing asthma and a method for evaluating an individual's propensity for cigarette consumption. These methods include obtaining a nucleic acid molecule sample from said individual. The methods further include determining whether a polymorphism in a nucleic acid sequence of the gene encoding coumarin 7-hydroxylation protein is present in the nucleic acid sample, wherein the polymorphism is selected from: a T for C substitution corresponding to position 202 of SEQ ID NO:21; a C for T substitution corresponding to position 369 of SEQ ID NO:21; an A for G substitution corresponding to position 394 of SEQ ID NO:21; an A for C substitution corresponding to position 413 of SEQ ID NO:21; a G for T substitution corresponding to position 743 of SEQ ID NO:21; and an A for G at position 841 of SEQ ID NO:21

The methods of the present invention can further include determining whether an individual is homozygous or heterozygous for a given nucleic acid sequence. Such methods can be either a cDNA assay and a genomic DNA assay. Such methods can also include a step of digesting a nucleic acid molecule with a restriction enzyme that distinguishes between a polymorphic nucleic acid sequence and the corresponding wildtype sequence. Further, the methods can include amplifying a selected region of the nucleic acid molecule of the individual.

Additional embodiments of the present invention include kits for conducting the various methods. Such kits can include nucleic acid molecules of the present invention, as well as restriction enzymes useful in the methods.

Further embodiments of the present invention include a computer for displaying nucleic acid sequence of a molecules of the present invention. Such a computer includes a computer-readable medium encoded with the nucleic acid sequence, to create an electronic file. The computer further includes hardware and software that display the nucleic acid sequence in the electronic file as a linear model of the molecule for analysis, alignment with other sequences or visualization of the nucleic acid sequence A further embodiment of the present invention is an isolated nucleic acid molecule comprising a nucleic acid sequence selected from SEQ ID NO:21 and a nucleic acid sequence that is fully complementary to SEQ ID NO:21.

A still further embodiment of the present invention is an isolated nucleic acid molecule having a nucleic acid sequence consisting essentially of a nucleic acid sequence selected from SEQ ID NO:9, SEQ ID NO:11, SEQ ID NO:13, SEQ ID NO:15, SEQ ID NO:17, and SEQ ID NO:19 and nucleic acid sequences that are fully complementary thereto.

DETAILED DESCRIPTION OF THE INVENTION

Figure 1:
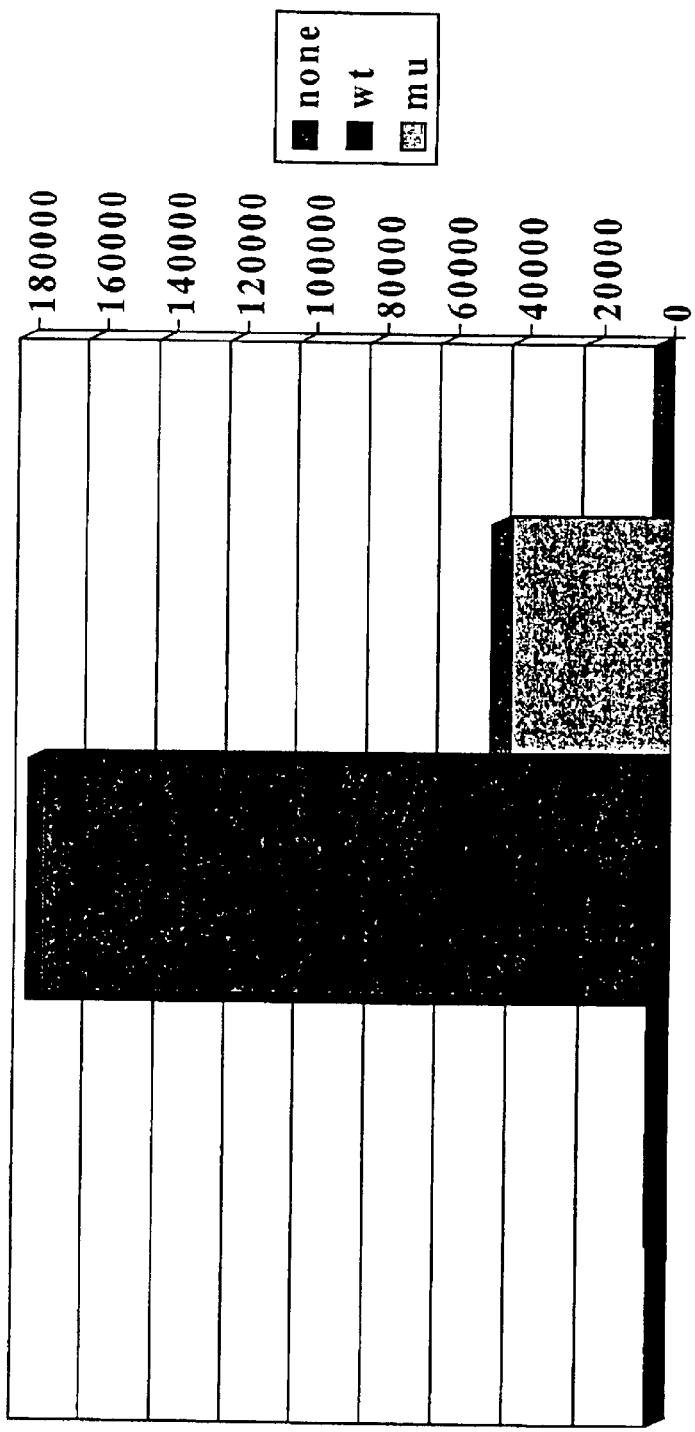
FIG. 1 illustrates the amount of luciferase activity detected using cell lines transfected with expression vector containing the wildtype CYP2A6, mutant CYP2A6 or no insert.

The present invention relates to compositions that contain certain genetic characteristics and methods that reveal the presence or absence of such characteristics. The present invention includes the identification of different genetic polymorphisms in the cytochrome P450 2A6 (CYP4502A6 or CYP2A6) gene. The presence or absence of the polymorphism at one or more of these sites has been found to be prognostic or diagnostic for inflammation, asthma or smoking. Nucleic acid molecules comprising the polymorphic sequences are used to screen individuals for altered metabolism for CYP2A6 substrates, potential drug—drug interactions, drug adverse side-effects, inflammation, asthma, susceptibility to habitual smoking, and diseases that result from environmental or occupational exposure to dangerous substances.

It is to be understood that the inventions disclosed herein are not limited to the particular methodology, protocols, cell lines, animal species or genera, constructs and reagents described, and as such may vary. It is also to be understood that the terminology used herein is for the purpose of describing particular embodiments only, and is not intended to limit the scope of the present invention which will be limited only by the appended claims.

For the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

According to the present invention, reference to an "isolated nucleic acid molecule" refers to a nucleic acid molecule which is the size of or smaller than a gene. Thus, an isolated nucleic acid molecule does not encompass isolated genomic DNA or an isolated chromosome. The term isolated nucleic acid molecule does not connote any specific minimum length. It should also be appreciated that reference to an isolated nucleic acid molecule does not necessarily reflect the extent of purity of the nucleic acid molecule. An isolated nucleic acid molecule of the present invention can be obtained from a natural source, such as a tissue sample, or it can be produced using molecular biology techniques, such as by PCR amplification, or it can be produced by chemical synthesis.

"Allele" has the meaning which is commonly known in the art, that is, a genomic variant of a referent gene, including variants, which, when translated result in functional or dysfunctional (including non-existant) gene products. The first identified allelic form is arbitrarily designated as the reference form and other allelic forms are designated as alternative or variant alleles. The allelic form occurring most frequently in a selected population is sometimes referred to as the wildtype form.

"Contiguously appurtenant to" means any bases flanking the referent position, including the instances of all bases selected 5' to the referent position and no bases selected 3' to the referent position; all bases selected 3' to the referent position and no bases selected 5' to the referent position; and some bases selected 5' and some bases selected 3' to the referent position. The term is intended to mean that the selected bases necessarily must be in the same sequential order as described in the referent sequence, with the exception of the variant base at the referent position.

"For the purpose of determining genotype" means that one of the purposes is to determine genotype, not necessarily that the end goal or use of the information is to determine genotype. For instance, "for the purpose of determining genotype" includes the use of the information to determine genotype for the ultimate goal of determining probability of negative or positive drug interactions.

"Gene" has the meaning that is commonly-known in the art, that is, a nucleic acid sequence that includes the translated sequences that code for a protein ("exons") and the untranslated intervening sequences ("introns"), and any regulatory elements ordinarily necessary to translate the protein.

"Genotype" has the meaning that is commonly-known in the art, that is, a physical description of a nucleic acid sequence.

"Hybridization" has the meaning that is commonly-known in the art, that is, the formation of a duplex structure by two single-stranded nucleic acids due to complementary base pairing. Hybridization can occur between exactly complementary nucleic acid strands or between nucleic acid strands that contain some regions of mismatch.

"Polymorphism" means a polymorphism wherein the group exists by virtue of a difference in identity of one or more nucleotides at given sequence locations. The location of nucleotide identity differences is usually preceded by and followed by highly conserved sequences (e.g., sequences that vary in less than $1/100$ or $1/1000$ members of the populations). However, more than one single nucleotide polymorphism can exist between or among the group members. A "transition" is the replacement of one purine by another purine or one pyrimidine by another pyrimidine. A "transversion" is the replacement of a purine by a pyrimidine or vice versa. Single nucleotide polymorphisms can also arise from a deletion of a nucleotide or an insertion of a nucleotide relative to a given sequence location.

"Stringent hybridization" means that which is commonly-known in the art, that is, at a salt concentration of no more than 1 M and a temperature of at least 25 degrees Celsius. For example, conditions of 5×SSPE (750 mM NaCl, 50 mM Sodium Phosphate, 5 mM EDTA, pH 7.4) and a temperature of 55 degrees to 60 degrees Celsius are suitable.

In the present invention, alleles are expressed by symbols in accordance with definitions given by IUPAC-IUB and common names or common usage in the art.

The wildtype CYP2A6 gene encodes an enzyme called coumarin 7-hydroxylase protein.

One embodiment of the present invention is an isolated nucleic acid molecule comprising a nucleic acid sequence selected from the group consisting of: a nucleic acid sequence comprising a nucleic acid sequence selected from the group consisting of SEQ ID NO:10, SEQ ID NO:12, SEQ ID NO:14, SEQ ID NO:16, SEQ ID NO:18, and SEQ ID NO:20; and a nucleic acid sequence that is fully complementary to such a nucleic acid sequence. In accordance with the present invention, an isolated nucleic acid molecule is a nucleic acid molecule that has been removed from its natural milieu (i.e., that has been subject to human manipulation) and can include DNA, RNA, or derivatives of either DNA or RNA. An isolated CYP2A6 nucleic acid molecule of the present invention can be isolated from its natural source or can be produced using recombinant DNA technology (e.g., polymerase chain reaction (PCR) amplification, cloning) or chemical synthesis. The CYP2A6 nucleic acid molecules of the present invention are isolated and obtained in substantial purity, generally as other than an intact chromosome. Usually, the nucleic acid molecule will be obtained substantially free of other nucleic acid sequences that do not include a CYP2A6 sequence or fragment thereof, generally being at least about 50%, usually at least about 90% pure. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably The nucleic acid sequence of the CYP2A6 genomic gene is generally known in the art and accessible in public databases as cited above. For example, GENEBANK® Accession No. U22027 identifies the human CYP4502A6 gene, although it contains some errors, as discussed below more fully in the Examples section. The sequence is useful as a reference for the genomic location of a polymorphism within the CYP2A6 gene or for specific CYP2A6 coding region sequences. As used herein, the term "CYP2A6 gene" is intended to refer to both the wildtype and polymorphic sequences, unless specifically denoted otherwise. Nucleic acids of particular interest comprise the provided polymorphic sequences. It is within the skill of one in the art to identify the location of a polymorphic sequence of the present invention using wildtype CYP2A6 genomic or cDNA sequences known in the art. A skilled artisan can use a polymorphic sequence, its corresponding wildtype sequence and the CYP2A6 sequence contiguously appurtenant to the referenced polymorphism provided in Table 3 with a known genomic sequence or cDNA sequence to determine the position of the polymorphism. It is within the scope of the invention that a polymorphism includes detection at the designated genomic sequence nucleotide position or its corresponding copy DNA (cDNA) position if the polymorphism is located within the coding region of the CYP2A6 sequence.

In accordance with the present invention, the polymorphisms of the CYP2A6 sequence occur at nucleotide −580, −413, −388, −369 or −39 of the promoter region of the CYP2A6 genomic sequence or nucleotide 51 of exon 1 of the CYP2A6 genomic sequence, with reference to the positions shown in the wild type sequence of SEQ ID NO.21, wherein positions 791–793 of SEQ ID NO:21 are nucleotides 1–3 of exon 1 (the initiation codon), and position 781, the transcription starting point, is nucleotide −1 of the promoter region. By identifying the location of the polymorphism at nucleotide 51 of the genomic sequence, it is within the skill of one in the art to determine the corresponding nucleotide number designation in the coding region of a cDNA sequence encoding coumarin 7-hydroxylase protein. These same polymorphisms correspond to nucleotide positions 202,369,394,413, 743 and 841, respectively, of SEQ ID NO:21. For the purposes of identification in this application, the positions of the polymorphisms of the present invention will be referenced as nucleotide positions 202, 369, 394, 413, 743 or 841.

In the case of positions −580, −413, −388, −369 or −39 of the promotor region or nucleotide 51 of exon 1, the polymorphism is typically one or more base pair substitutions such as C to T, T to C, G to A, C to A, T to G or G to A, respectively. The polymorphisms are silent and thus, the polymorphisms in the promoter region do not affect functioning of the promoter and the polymorphism in exon 1 does not result in an amino acid substitution.

Another embodiment of the present invention is an isolated nucleic acid molecule that comprises at least one base variation from that of a known human P450 sequence, wherein said nucleic acid molecule is selected from the group consisting of: (a) a nucleic acid molecule that comprises a T for a C at position 202 of SEQ ID NO:21 and at least 20 other bases, alternatively at least 30 other bases, at least 40 other bases or at least 50 other bases, of SEQ ID NO:21 contiguously appurtenant to said position; (b) a nucleic acid molecule which comprises a C for a T at position 369 of SEQ ID NO:21 and at least 20 other bases, alternatively at least 30 other bases, at least 40 other bases or at least 50 other bases, of SEQ ID NO:21 contiguously appurtenant to said position; (c) a nucleic acid molecule which comprises an A for a G at position 394 of SEQ ID NO:21 and at least 20 other bases, alternatively at least 30 other bases, at least 40 other bases or at least 50 other bases, of SEQ ID NO:21 contiguously appurtenant to said position; (d) a nucleic acid molecule which comprises an A for a C at position 413 of SEQ ID NO:21 and at least 20 other bases, alternatively at least 30 other bases, at least 40 other bases or at least 50 other bases, of SEQ ID NO:21 contiguously appurtenant to said position; (e) a nucleic acid molecule which comprises a G for a T at position 743 of SEQ ID NO:21 and at least 20 other bases, alternatively at least 30 other bases, at least 40 other bases or at least 50 other bases, of SEQ ID NO:21 contiguously appurtenant to said position; (f) a nucleic acid molecule which comprises an A for a G at position 841 of SEQ ID NO:21 and at least 20 other bases, alternatively at least 30 other bases, at least 40 other bases or at least 50 other bases, of SEQ ID NO:21 contiguously appurtenant to said position; or (g) a nucleic acid which is fully complementary to a nucleic acid molecule of (a) through (f). In this embodiment, the isolated nucleic acid molecule can be defined, in part, by comprising a nucleic acid sequence selected from SEQ ID NO:10, SEQ ID NO:12, SEQ ID NO:14, SEQ ID NO:16, SEQ ID NO:18, or SEQ ID NO:20.

Preferred CYP2A6 nucleic acid molecules include nucleic acid molecules having a nucleic acid sequence that is at least about 80%, more preferably at least about 85%, more preferably at least about 90%, more preferably at least about 95%, and more preferably at least about 98% identical to nucleic acid sequence SEQ ID NO:10, SEQ ID NO:12, SEQ ID NO:14, SEQ ID NO:16, SEQ ID NO:18, and/or SEQ ID NO:20.

As used herein, unless otherwise specified, reference to a percent (%) identity refers to an evaluation of homology which is performed using: (1) a BLAST 2.0 Basic BLAST homology search using blastn for nucleic acid searches with standard default parameters, wherein the query sequence is filtered for low complexity regions by default (described in Altschul, S.F., Madden, T.L., Schäafer, A.A., Zhang, J., Zhang, Z., Miller, W. & Lipman, D.J. (1997) "Gapped BLAST and PSI-BLAST: a new generation of protein database search programs." Nucleic Acids Res. 25:3389–3402, incorporated herein by reference in its entirety); (2) a BLAST 2 alignment (wing to parameters described below); or (3) both BLAST 2.0 and BLAST 2. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify to second sequence in the top matches. Therefore, it is to be understood that percent identity can be determined by using either one or both of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247–250, incorporated herein by reference in its entirety. BLAST 2 sequence alignment is performed in blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:

Reward for match=1

Penalty for mismatch=−2

Open gap (5) and extension gap (2) penalties gap x_dropoff (50) expect (10) word size (11) filter (on)

In some embodiments, as indicated, to align and calculate the percent identity between two amino acid sequences, the Martinez/Needleman-Wunsch DNA alignment method is used. This method is provided by the Lasergene MegAlign, a module within the DNASTAR program (DNASTAR, Inc., Madison, Wis.), and the standard default parameters are used as follows:

(1) Minimum match=9;

(2) Gap penalty=1.10;

(3) Gap length penalty=0.33.

Another preferred nucleic acid molecule of the present invention includes at least a portion of nucleic acid sequence SEQ ID NO:10, SEQ ID NO:12, SEQ ID NO:14, SEQ ID NO:16, SEQ ID NO:18, and/or SEQ ID NO:20, that is capable of hybridizing to a CYP2A6 gene and includes of an allelic variation of the wild type CYP2A6 gene. A more preferred nucleic acid molecule includes the nucleic acid sequence SEQ ID NO:10, SEQ ID NO:12, SEQ ID NO:14, SEQ ID NO:16, SEQ ID NO:18, and/or SEQ ID NO:20. Such nucleic acid molecules can include nucleotides in addition to those included in the SEQ ID NOs, such as, but not limited to, a full-length gene or a full-length coding region.

The present invention also includes nucleic acid molecules that are oligonucleotides capable of hybridizing, under stringent hybridization conditions, with complementary regions of other, preferably longer, nucleic acid molecules of the present invention such as those comprising CYP2A6 genes or other CYP2A6 nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules or primers to produce nucleic acid molecules. Also provided are oligonucleotides that can be used as primers to amplify DNA from a variant or a wildtype CYP2A6 nucleic acid molecule. Preferred oligonucleotide probes or primers include a single base change of a polymorphism of the present invention or the wildtype nucleotide that is located at the same position. Preferably the nucleotide of interest occupies a central position of a probe. Preferably the nucleotide of interest occupies a 3' position of a primer.

The minimal size of a nucleic acid molecule of the present invention Is a size capable of forming a stable hybrid (i.e., hybridize under stringent hybridization conditions) with the complementary sequence of a nucleic acid molecule encoding a coumarin 7-hydroxylaso natural protein. As such, the size of the nucleic acid molecule is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 15 to about 18 bases in length. Unless specified otherwise, there is no limit, other than a practical limit, on the maximal size of such a nucleic acid molecule in that the nucleic acid molecule can include a portion of a gene, an entire gene, multiple genes, or portions thereof. In preferred embodiments, however, nucleic acid molecules of the present invention are typically less than about 5 kilobases in length and more preferably less than about 70 nucleotides in length. For instance, the present invention includes human CYP2A6 alleles that comprise base pair changes as described herein, having appurtenant sequences, based on either SEQ ID NO:21 or GENEBANK® Accession No. U22027, of 10, 15, 20, 25, 30, 35, 45, 50, 55, 60, 65, 70, 75, 80, 85, 90,95, 100, 105, 110, 115, 120, 125, 130, 135, 140, 145, 150, 155, 160, 165, 170, 175, 180, 185, 190, 195, 200, 250, 300, 350, 400, 450, 500, or 1000 bases, or any whole number encompassed by the range of 10–10,000.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch (e.g., 80%, 85%, 90%, 95%, or 98%) of nucleotides are disclosed, for example, in Meinkoth et al., 1984,*Anal. Biochem.* 138, 267–284; Meinkoth et al., ibid., is incorporated by reference herein in its entirety.

The genotype of an individual is determined with respect to the provided CYP2A6 gene polymorphisms. The genotype is useful for determining the presence of phenotypically evident polymorphism, and for determining the linkage of a polymorphism to a phenotypic change.

One embodiment of the present invention is a method of identifying a sample containing a nucleic acid molecule that comprises a wildtype or variant allele, the method comprising identifying the presence or absence of one or more polymorphisms in a sequence of a gene that is capable of encoding coumarin 7-hydroxylase.

Another embodiment of the present invention is a method for identifying whether a sample containing a nucleic acid molecule is associated with inflammation and/or asthma, the method comprising identifying the presence or absence of one or more CYP2A6 alleles, wherein the pattern of alleles is indicative of inflammation and/or asthma.

Another embodiment of the present invention is a method of identifying a sample containing a nucleic acid molecule that is associated with inflammation and/or asthma, the method comprising identifying the presence or absence of a polymorphism in the nucleic acid sequence encoding coumarin 7-hydroxylase protein, wherein said polymorphism is indicative of protection against developing inflammation and/or asthma.

Another embodiment of the present invention is a method of identifying a sample containing a nucleic acid molecule is associated with the occurrence of smoking, the method comprising identifying the presence or absence of a polymorphism in the nucleic acid sequence encoding coumarin 7-hydroxylase protein, wherein said polymorphism is prognostic for habitual smoking.

The invention provides a variety of assays for identifying individuals having one or more wild type or variant alleles. The assays identify polymorphisms in CYP2A6 cDNA or CYP2A6 genomic DNA (i.e., including the entire CYP2A6 gene and not just the coding region), which is the principal human determinant of coumarin 7-hydroxylase activity. Such assays are referred to herein as "cDNA assays" and "genomic DNA assays." It should be noted that genomic DNA assays include not only analysis of actual genomic DNA derived from a natural source, but also analysis of any amplification product or other derivative (e.g., restriction fragments) of genomic DNA derived from a natural source. The cDNA assays are particularly useful for de novo localization of a CYP2A6 polymorphism to a particular nucleotide or nucleotides. The genomic assays are particularly useful for rapid screening of individuals for the presence of a polymorphism.

Many of the diagnostic assays rely on amplification of part or all of a CYP2A6 nucleic acid molecule. In one embodiment, portions of a CYP2A6 nucleic acid molecule are amplified by the polymerase chain reaction (PCR). The PCR process is described in e.g., U.S. Pat. Nos. 4,683,195; 4,683,202; and 4,965,188; PCR Technology:Principles and Applications for DNA Amplification (ed. Erlich, Freeman Press, New York, N.Y., 1992); PCR Protocols: A Guide to Methods and Applications (eds. Innis et al., Academic Press, San Diego, Calif. (1990); Mattila et al. Nucleic Acids Res. 19:4967 (1991); Eckert & Kunkel PCR Methods and Applications 1:17 (1991); PCR (eds. McPherson et al., IRL Press, Oxford), each of which is incorporated by this reference in its entirety.

To amplify a portion of a CYP2A6 nucleic acid molecule in a sample by PCR, the sequence must be accessible to the components of the amplification system. Accessibility can be achieved by isolating nucleic acid molecules from the sample. A variety of techniques for extracting nucleic acid molecules from biological samples are known in the art. Alternatively, if the sample is fairly readily disruptable, the nucleic acid need not be purified prior to amplification by the PCR technique, i.e., if the sample is comprises cells, particularly peripheral blood lymphocytes or monocytes, lysis and dispersion of the intracellular components may be accomplished merely by suspending the cells in hypotonic buffer. See Han et al., Biochemistry, 1987, vol. 26, pages 1617–1625. Polymorphisms are detected in a nucleic acid molecule from an individual being analyzed. For assay of genomic DNA, virtually any biological sample (other than pure red blood cells) is suitable. Examples of convenient tissue samples include whole blood, semen, saliva, tears, urine, fecal material, sweat, buccal, skin and hair. Nucleic acid molecules can be obtained according to procedures well-known in the art.

For amplification of mRNA sequences, a first step is the synthesis of a DNA copy (cDNA) of the region to be amplified by reverse transcription. Reverse transcription is the polymerization of deoxynucleoside triphosphates to form primer extension products that are complementary to a ribonucleic acid template. The process is effected by reverse transcriptase, an enzyme that initiates synthesis at the 3'-end of the primer and proceeds toward the 5'-end of the template until synthesis terminates. Examples of suitable polymerizing agents that convert the RNA nucleic acid molecule into a complementary, copy-DNA (cDNA) sequence are avian myeloblastosis virus reverse transcriptase and *Thermus thermophilous* DNA polymerase. Reverse transcription can be carried out as a separate step, or in a homogeneous reverse transcription-polymerase chain reaction (RT-PCR). Polymerizing agents suitable for synthesizing a cDNA sequence from the RNA template are reverse transcriptase (RT), such as avian mycloblastosis virus RT, Moloney murine leukemia virus RT, or *Thermus thermophilous* DNA polymerase.

Primers for PCR amplification are designed so that the position at which each primer hybridizes along a duplex sequence is such that an extension product synthesized from one primer, when separated from the template (complement), serves as a template for the extension of the other primer. The primers are selected to be substantially complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer with the remainder of the primer sequence being complementary to the strand. Alternatively, complementary bases or longer sequences can be interspersed into the primer, provided that the primer sequence has sufficient complementarity with the sequence of the strand to be amplified to hybridize therewith and thereby form a template for synthesis of the extension product of the other primer. Paired primers for amplification of a given segment of DNA are designated forward and reverse primers. The forward primer hybridizes to a double-stranded DNA molecule at a position 5', or upstream, from the reverse primer. The forward primer hybridizes to the complement of the coding strand of the double stranded sequence, i.e., the antisense strand, and the reverse primer hybridizes to the coding strand.

The appropriate length of a primer depends on the intended use of the primer but typically ranges from about 10 to about 100, preferably about 15 to about 50, more preferably about 15 to about 35, or more preferably about 20 to about 30 nucleotides in length. The spacing of primers determines the length of segment to be amplified. The spacing is not usually critical and amplified segments can range in size from about 25 bases to at least about 35 kilobases in length. Segments from about 25 to about 2000, preferably about 50 to about 1000, more preferably about 100 to about 500 nucleotides in length are typical.

A primer can be labeled, if desired, by incorporating a label detectable by spectroscopic, photochemical, biochemical, immunochemical, or chemical means. For example, useful labels include .sup.32 P, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

Other suitable amplification methods include the ligase chain reaction (LCR) (see Wu and Wallace, Genomics, 1989, vol. 4, pages 560–569; Landegren et al., Science, 1988, vol. 241, pages 1077–1080; transcription amplification (Kwoh et al, Proc. Natl. Acad. Sci. USA, 1989, vol. 86, pages 1173–1177), and self-sustained sequence replication (Guatelli et al., Proc. Nat. Acad. Sci. USA, 1990, vol. 87, pages 1874–1878) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

An allele-specific primer can be used in a PCR amplification. The allele-specific primer hybridizes to a site on a nucleic acid molecule that overlaps with a polymorphism and extension will only occur if an allelic form complementary to the primer is present. See Gibbs, Nucleic Acid Res., 1989, vol. 17, pages 2427–2448. This primer is used in conjunction with a second primer which hybridizes at a distal site. Amplification proceeds from the two primers leading to a detectable product signifying the particular allelic form is present. Thus, the presence or absence of an amplification product is detected using standard methods. Controls can be used that test the efficacy of the amplification reaction itself or that allow the experimental results to be compared with known wildtype or polymorphic CYP2A6 nucleic acid molecule samples. The method works best when the mismatch is included in the 3'-most position of the oligonucleotide aligned with the polymorphism because this position is most destabilizing to elongation from the primer.

Sample nucleic acid molecules, isolated directly from cells, amplified or cloned fragments, can also be analyzed by a number of other methods known in the art. The nucleic acid molecule can be sequenced by using either the dideoxy chain termination method or other methods (see for example Sambrook et al., Molecular Cloning, A Laboratory Manual (2nd Ed., CSHP, New York 1989); Zyskind et al., Recombinant DNA Laboratory Manual, (Acad. Press, 1988)).

Hybridization using allele-specific probes, described by e.g., Saiki et al., Nature 324, 163–166 (1986); Dattagupta, EP 235,726, Saiki, WO 89/11548, can be used to determine the presence or absence of a polymorphism by, for example Southern blot, dot blots, etc. An allele-specific probe can be designed that hybridizes to a segment of a nucleic acid molecule from one individual but does not hybridize to the corresponding segment from another individual due to the presence of different polymorphic forms in the two individuals. Hybridization conditions should be sufficiently stringent that there is a significant difference in hybridization intensity between alleles.

The hybridization pattern of a control and variant sequence to an array of oligonucleotide probes immobilized on a solid support, as described in U.S. Pat. No. 5,445,934, or in WO 95/35505, can also be used as a means of detecting the presence of variant sequences.

Amplification products generated using the polymerase chain reaction can be analyzed by the use of denaturing gradient gel electrophoresis (DGGE). Different alleles can be identified based on the different sequence-dependent melting properties and electrophoretic migration of DNA in solution. Erlich, ed., PCR Technology, Principles and Applications for DNA Amplification, (W. H. Freeman and Co, New York, 1992), Chapter 7.

Alleles of target sequences can be differentiated using single-strand conformation polymorphism analysis (SSCP), which identifies base differences by alteration in electrophoretic migration of single stranded PCR products, as described in Orita et al., Proc. Nat. Acad. Sci. 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

Other methods of detection include mismatch cleavage detection and heteroduplex analysis in gel matrices. These methods are used to detect conformational changes created by DNA sequence variation as alterations in electrophoretic mobility. Alternatively, where a polymorphism creates or destroys a recognition site for a restriction endonuclease, referred to as restriction length polymorphism, or RFLP, the sample is digested with that endonuclease and the products size fractionated to determine whether the fragment was digested. Fractionation is performed by gel or capillary electrophoresis, particularly acrylamide or agarose gels.

In one embodiment of the present invention, an array of oligonucleotides are provided, where discrete positions on the array are complementary to one or more of the provided polymorphic sequences, e.g. oligonulcoetides of at least 12 nucleotides, frequently 20 nucleotides or larger and including the sequence flanking the polymorphic position. Such an array may comprise a series of oligonucleotides, each of which can specifically hybridize to a different polymorphism. For examples of arrays, see Hacia et al., 1996, Nat. Genet., vol. 14, pages 441–447 and DeRisi et al., 1996, Nat. Genet., vol. 14, pages 457–460. Arrays of interest may further comprise sequences, including polymorphisms, of other genetic sequences, particularly other sequences of interest for pharmacogenetic screening.

It is within the scope of the present invention that one or more CYP2A6 polymorphisms provided herein can be detected in a single assay such as a multiplex assay to identify the presence or absence of different alleles in the same assay, see for example Stuven et al., Pharmacogenetics, 1996, vol. 6, pages 417–421.

According to the present invention, a polymorphism provided herein is indicative of protection against developing inflammation and/or asthma. The presence of a polymorphism of the present invention in the CYP2A6 gene is capable of protecting an individual against developing inflammation and/or asthma. Thus, the absence of a polymorphism of the present invention in the CYP2A6 gene is predictive of inflammation and/or asthma development. A polymorphism of the present invention is also prognostic for habitual smoking. The absence of a polymorphism of the present invention in the CYP2A6 gene is predictive of habitual smoking.

An example of a polymorphism of the present invention, the presence or absence of which is predictive of inflammation and/or asthma or habitual smoking in individuals is designated the 743 polymorphism. See Examples 4 and 5. The 743 polymorphism results from a single-base mutation in genomic CYP2A6 DNA at nucleotide position −39 of the promoter region. The nucleotide corresponds to nucleotide 743 in SEQ ID NO:21. The 743 polymorphism results in a T to G transposition. The 743 polymorphism at this position occurs in all ethnic groups studied at varying frequencies. See Example 2. Coumarin 7-hydroxylase is found in human lung. Without being bound by theory, Applicants believe that the coumarin 7-hydroxylase in lung is capable of metabolizing environmental substances that enter the lung. Upon metabolism, the environmental substances can irritate airway tissue resulting in inflammation of such tissue and/or asthma. The polymorphism at position 743 of SEQ ID NO:21 disrupts the expression of the CYP2A6 gene, thereby decreasing the production of coumarin 7-hydroxylase. Thus, Applicants believe that individuals polymorphic at position 743 produce lower levels of coumarin 7-hydroxylase, thereby lowering the production of environmental irritants in their lungs that can result in inflammation or asthma.

A preferred strategy for analysis entails amplification of a DNA sequence spanning the 743 polymorphism. Amplification of such a sequence can be primed from forward and reverse primers that hybridize to a CYP2A6 gene on opposite sides of the 743 polymorphism but which do not hybridize to the variant nucleotide itself. That is, for detection of the 743 polymorphism, the forward primer hybridizes upstream or 5' to the 743 nucleotide and the reverse primer hybridizes downstream or 3' to this nucleotide. The forward primer is sufficiently complementary to the antisense strand of a CYP2A6 nucleic acid molecule to hybridize therewith and the reverse primer is sufficiently complementary to the sense strand of the CYP2A6 sequence to hybridize therewith. The primers usually comprise first and second subsequences from opposite strands of a double-stranded CYP2A6 DNA sequence. It is particularly important to avoid mismatches in the two nucleotides at the 3' end of the primer (especially the terminal nucleotide).

For amplification of the 743 polymorphism, forward primers preferably comprise a segment of contiguous nucleotides from the promoter region and reverse primers a segment of contiguous nucleotides from the intron 1 region.

Preferred primers exhibit perfect sequence identity to CYP2A6 and lesser sequence identity to corresponding regions of related genes, such as CYP2A7 and CYP2A13. Such primers are designed by comparison of the wildtype CYP2A6 sequence with corresponding sequences from CYP2A7 and CYP2A13. An exemplary pair of primers for amplifying a segment spanning the 743 mutation is described in Example 1, such as SEQ ID NO:1 and SEQ ID NO:2. The amplification product from these primers has a length of 988 bp.

Having amplified a segment of a CYP2A6 gene known to span the 743 polymorphism, a variety of assays are available for determining whether the 743 polymorphism is present that are disclosed herein, preferably, using allele specific primers. For example, selective amplification of the wildtype allele of the CYP2A6 allele can be accomplished using a forward primer that has about 10–50, and usually 15–30 nucleotides from the wildtype CYP2A6 genomic sequence, including nucleotide 743. Such a forward primer when paired with any suitable reverse primer downstream from nucleotide 743 (i.e., sufficiently complementary to the sense strand of CYP2A6 to hybridize therewith) can be used to amplify selectively the wildtype allele without amplifying a mutant allele. The 743 nucleotide usually occurs near, or preferably, at the 3' end of the primer. The same result can be achieved by using a reverse primer that has about 10–50 or usually 15–30 contiguous nucleotides from the complement of the wildtype CYP2A6 genomic sequence (i.e., the antisense strand) including the nucleotide at position 743. Such a reverse primer can be paired with any suitable forward primer sufficiently complementary to a sequence of the antisense strand of the CYP2A6 gene upstream from nucleotide 743 to hybridize therewith. The 743 nucleotide should again be at or near the 3' end of the reverse primer. For selective amplification of a 743 mutant allele a suitable forward primer for amplification comprises about 10–50 or usually 15–30 contiguous nucleotides including nucleotide 743 from the mutant CYP2A6 genomic sequence (i.e., the sense strand). The forward primer can be paired with any suitable reverse primer sufficiently complementary to the sense strand of a CYP2A6 genomic subsequence downstream from nucleotide 743 to hybridize therewith. Alternatively, the same result can be achieved using a reverse primer comprising about 10–50 or 15–30 contiguous nucleotides including nucleotide 743 from the complement of the mutant CYP2A6 sequence (i.e., the antisense strand). Such a reverse primer can be paired with any suitable forward primer sufficiently complementary to the antisense strand of a CYP2A6 subsequence upstream from nucleotide 743 to hybridize therewith.

Following amplification, the sample under test is characterized as wildtype or mutant by the presence or absence of an amplification product. With a primer designed for selective amplification of the wildtype allele, the presence of an amplification product is indicative of that allele and the absence of an amplification product indicative of a mutant allele. The converse applies for primers designed for selective amplification of a mutant allele. In preferred assay, a sample is divided into two aliquots, one of which is amplified using primers for wildtype allele amplification, the other of which is amplified using primers appropriate for mutant allele amplification. The presence of an amplification product in one but not both of the aliquots indicates that the individual under test is either wildtype or a homozygous for the mutation (depending on aliquot in which the amplification product occurred). The presence of amplification product in both aliquots indicates that the individual is heterozygous. The absence of an amplification product in both aliquots would indicate either the absence of a CYP2A6 gene or a quality control problem in the amplification procedure requiring that the assay be repeated. The presence or absence of amplification products can be detected by gel electrophoresis using methods standard in the art or described herein.

One embodiment of the present invention is a diagnostic kit. The kit comprises useful components for practicing the methods of the present invention. The kit typically comprises at least one of the primers needed for the PCR amplification if PCR amplification is used and also control DNA suitable for determining the success of the PCR reaction and/or to confirm the identification of the presence or absence of a polymorphism in a sample. A kit usually contains a matched pair of forward and reverse primers as described above for amplifying a segment encompassing a polymorphism of the present invention. For selective amplification of mutant or wildtype alleles, kits usually contain a pair of primers for amplification of the mutant allele and/or a separate pair of primers for amplification of the wildtype allele. Optional additional components of the kit include, for example, restriction enzymes for analysis of amplification products, reverse-transcriptase or polymerase, the substrate nucleoside triphosphates, and the appropriate buffers for reverse transcription, PCR, or restriction enzyme reactions. Usually, the kit also contains instructions for carrying out the methods.

The method of the present invention is characterized by detecting the polymorphisms provided herein, and is useful in gene diagnosis for detecting CYP2A6 gene polymorphisms. As long as the method is capable of detecting the aforementioned specific types of mutation which are clearly defined and characterized by the present invention, no limitation is imposed on the technique, etc. to be employed in the method. For example, a variety of routine methods may be widely used. Since the types of gene mutation to be detected by the present invention are now clarified and specified, it would be obvious for skilled persons in the art to adopt a suitable method for detecting them from the reading of the disclosure of this specification.

Also provided by the present invention are methods for detecting a polymorphic sequence of the P450 gene in a sample containing human nucleic acid molecules comprising identifying the presence or absence of a polymorphism that correlates with the nucleic acid sequence identified at positions 202, 369, 394, 413, 743 or 841 of SEQ ID NO:21. In one embodiment, said method further comprises: (a) mixing said nucleic acid molecules with one or more second nucleic acid molecules of the present invention so as to form a mixture; (b) subjecting said mixture to hybridization conditions; and (c) detecting any hybrids formed. Those methods wherein said nucleic acid is amplified prior to step (a) are preferred. The materials useful for these methods can be obtained as described, and these methods can be accomplished as discussed. In a preferred embodiment, the second nucleic acid molecule consists of a primer of the present invention and step (c) is accomplished by determining the presence or absence of a PCR product. In another preferred embodiment, the second nucleic acid molecule is a probe of the present invention, wherein the probe is labeled with a detectable marker and step(c) is accomplished by determining the presence or absence of the detectable marker.

In other embodiments, methods of the present invention comprise digesting DNA comprising at least a part of the nucleic acid sequence containing the polymorphic site with a restriction enzyme that will cut, or will not cut, at or adjacent to one of the polymorphic positions according to whether the polymorphism is present. In this manner, such restriction enzymes distinguish between wildtype and mutant alleles. Those methods wherein said nucleic acid is amplified prior to the digestion step are preferred. The materials useful for these methods can be obtained as described, and these methods can be accomplished as discussed.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

Another embodiment of the present invention includes a computer for displaying a nucleic acid sequence of a molecule of the present invention, as broadly described herein. Such a computer includes a computer-readable medium encoded with one or more of said nucleic acid sequences to create an electronic file. The computer further includes hardware and software that display the nucleic acid sequence in the electronic file as a linear model of the molecule for analysis, alignment with other sequences or visualization of the nucleic acid sequence by the computer. Such hardware and software components are well-known in the art. Also provided are databases comprising sequence information pertaining to nucleic acid molecules of the present invention.

EXAMPLES

Example 1

This example describes the identification of variants of the known cytochrome P450 2A6 sequence (CYP4502A6).

Blood specimens from 32 individuals were collected after obtaining informed consent. All samples were stripped of personal identifiers to maintain confidentiality. The only data associated with the sample were self-reported gender and racial group designations. Of the 32 individuals, 10 were African Americans, 10 were Caucasians, 6 were Japanese and 6 were Chinese. Genomic DNA was isolated using standard methods.

Polymerase chain reaction amplification of regions of the CYP4502A6 gene were performed using the primers listed in Table 1. Each polymerase chain reaction (PCR) amplification was performed in a total reaction volume of 100 microliters ($\mu$l). The final magnesium chloride concentration for each reaction was optimized empirically and is shown in Table 1. The final genomic DNA concentration was about 100 nanogram (zig) per reaction from 2 individuals. The PCR reactions were performed using Perkin Elmer's GENEAMP® PCR kit (available from Perkin Elmer, Norwalk, CN) using Taq Gold DNA polymerase according to manufacturer's instructions and using the following primers.

TABLE 1

PCR Primers and Mg++ Concentration

| Region | Forward/Reverse | SEQ ID NO: | 5'-3' | [Mg++] |
|--------|-----------------|------------|-------|--------|
| 2A6 | F | 1 | TTCCCCTGAAATATGG | 2 mM |
| 2A6 | R | 2 | CTTCTCCCTGTCTTGG | 2 mM |

Thermal cycling was performed with an initial denaturation step at 95° C. for 10 min, followed by 35 cycles of denaturation at 95° C. for 30 sec, primer annealing at 55° C. for 45 see, and primer extension at 72° C. for 2 min, followed by final extension at 72° C. for 5 min.

The resulting PCR product were purified using MICROCON®-100 columns (available from Millipore, Bedford, Mass. PCR products from two individuals were combined for each cycle of sequencing. Cycle sequencing was performed on the GENEAMP®-PCR System 9600 PCR machine using the ABI PRISM® dRhodamine Terminator Cycle Sequencing Ready Reaction Kit (available from Applied Biosystems, Inc., Foster City. Calif.) according to the manufacturer's directions. Oligonucleotide primers used for the sequencing reactions include SEQ ID NO:1 and those shown in Table 2.

TABLE 2

Sequencing Primers

| Region | Forward/Reverse | SEQ ID NO: | 5'-3' |
|--------|-----------------|------------|-------|
| 2A6(1) | F | 3 | TTCCCCTGAAATATGG |
| 2A6(2) | F | 4 | GCCACACTTTGTCTTACC |
| 2A6(3) | F | 5 | TGGGGCTTGTAGTTGG |
| 2A6(1) | R | 6 | CTGTTGTGGAGGATGC |
| 2A6(2) | R | 7 | GGTCTGTGGTACTTCAGGAG |
| 2A6(3) | R | 8 | CAATGAAGGGCAATGG |

About 8 $\mu$l sequencing reactions were subjected to 30 cycles at 96° C. for 20 sec, 50° C. for 20 sec, and 60° C. for 4 min, followed by ethanol precipitation. Samples were evaporated to dryness at 50° C. for about 15 min and resuspended in 2 $\mu$l of loading buffer (5:1 deionized formamide:50 mM EDTA pH 8.0), heated to 65° C. for 5 min, and electrophoresed through 4% polyacrylamide/6M urea gels in an ABI 377 Nucleic Acid Analyzer according to the manufacturer's instructions to obtain sequence information. All sequences were determined from both the 5' and 3' (sense and antisense) direction. The 16 electropherograms were analyzed by comparing peak heights, looking for about 25% reduction in peak size and/or presence of extra peaks as an indication of heterozygosity.

Portions of the CYP4502A6 sequence including a single nucleotide polymorphism identified from the sequencing are shown below the corresponding portions of the wildtype sequence, with the position of the polymorphism shown in bold, in Table 3. For example, a variation of a C to a T transition was discovered at base pair −580 in the promoter region of the CYP4502A6 gene.

TABLE 3

Newly Identified CYP4502A6 Gene Polymorphisms

| Location | Position in SEQ ID NO:21 | SEQ ID NO | Polymorphism Sequence |
|---|---|---|---|
| Promoter −580 | 202 | 9 | GAACCCGCTGGGCTT |
|  |  | 10 | GAACCCGTTGGGCTT |
| Promoter −413 | 369 | 11 | ACTTTGTCTTACCCTAA |
|  |  | 12 | ACTTTGTCTCACCCTAA |
| Promoter −388 | 394 | 13 | GACCTTTGGATTCCTCT |
|  |  | 14 | GACCTTTGAATTCCTCT |
| Promoter −369 | 413 | 15 | CCCTGGAACCCCCAGATC |
|  |  | 16 | CCCTGGAACACCCAGATC |
| Promoter −39 | 743 | 17 | CAGGCAGTATAAAGGCAA |
|  |  | 18 | CAGGCAGTAGAAAGGCAA |
| Exon 1  51 | 841 | 19 | CCTGACTGTGATGGTCT |
|  |  | 20 | CCTGACTGTAATGGTCT |

SEQ ID NO:21 lists the sequence of the reference CYP4502A6 gene, including promoter, exons 1 and 2 and correction of some errors that were present in the GENEBANK® Accession No. U22027.

Example 2

This example describes genotype frequencies for a CYP4502A6 promoter variant in different ethnicities.

Genotyping of 32 individuals from each of 4 broadly defined racial groups (Caucasian, African American, Hispanic and Asian American) for one polymorphism produced the allele and genotype frequencies shown in Table 4.

TABLE 4

CYP4502A6 Promoter Variant and Ethnic Frequencies.

| Racial Group | Allele A (wild type) | B (mutant) | n |
|---|---|---|---|
| Caucasian | 0.94 | 0.06 | 573 |
| African American | 0.89 | 0.11 | 236 |
| Hispanic | 0.89 | 0.11 | 300 |
| Asian American | 0.77 | 0.23 | 72 |

The results indicate that the variant allele, a guanine residue at position −39 in the promoter of CYP4502A6, occurs in all ethnic groups studied but at different frequencies among the groups.

Example 3

This example describes the comparison of expression of a luciferase gene using promoter regions comprising CYP4502A6 wildtype promoter sequence and CYP4502A6 promoter sequence containing a polymorphic site.

Two different recombinant molecules, one containing the promoter region from the wildtype allele and the other from the mutant allele of CYP4502A6 operatively linked to the luciferase gene transcription control sequences were produced as follows. An about 744-nucleotide DNA fragment (SEQ ID NO:22) comprising the CYP4502A6 promoter region from the wildtype allele, denoted herein as 2A6WT$_{744}$, was PCR amplified from 50 ng of genomic DNA isolated from individuals known to have the wildtype allele, using a sense primer having the nucleic acid sequence 5' AAGCTTAGAAGATGGCAGTGGAG 3' (SEQ ID NO:23) that includes a Hind III site at the 3' end, and an antisense primer having the nucleic acid sequence 5' GAGCTCGGTGGTAGAGGGATG 3' (SEQ ID NO:24) that includes a Sac I site at the 3' end. The PCR product was used directly for subcloning into the TA vector pCR2. I (available from Invitrogen, Carlsbad, Calif.) producing the recombinant molecule p 2A6WT$_{744}$.

An about 744-nucleotide DNA fragment (SEQ ID NO:25) comprising the CYP4502A6 promoter region from the allele containing the polymorphic site at position −39 of the promoter region, denoted herein as 2A6SNP$_{744}$, was PCR amplified from 50 ng of genomic DNA isolated from individuals known to have the mutant allele, using sense primer SEQ ID NO:23 and antisense primer SEQ ID NO:24. The PCR product was used directly for subcloning into the TA vector pCR2.1 (available from Invitrogen, Carlsbad, Calif.) producing the recombinant molecule p 2A6SNP$_{744}$.

Both the promoter region 2A6WT$_{744}$ and 2A6SNP$_{744}$ were then subcloned separately into an expression vector containing a luciferase gene. Recombinant molecule p2A6WT$_{744}$luc was produced by digesting 2A6WT$_{744}$ with HindIII and SacI restriction endonucleases, column purifying the resulting fragment, and directionally subcloning the fragment into expression vector p20LUC (van Zonneveld et al., 1988, PNAS 85:5525–9). Recombinant molecule p2A6SNP$_{744}$luc was produced by digesting 2A6SNP$_{744}$ with the same restriction enzymes and directionally subcloning the fragment into the p20LUC expression vector.

Recombinant molecules p2A6WT$_{744}$luc and p2A6SNP$_{744}$luc were each transformed into a human carcinoma cell line (available from ATCC), a human lymphoblast cell line (available from Coriell Cell Repository) and a Chinese hamster ovary cell line (available from ATCC) using standard techniques to form recombinant cells HEP-p2A6WT$_{744}$luc cells, HEP-p2A6SNP$_{744}$luc cells, LB-p2A6WT$_{744}$luc cells, LB-p2A6SNP$_{744}$luc cells, CHO-p2A6WT$_{744}$luc cells and CHO-p2A6SNP$_{744}$luc cells, respectively. Each transfection experiment was done in triplicate. Cells were also transfected with control vectors including a control vector constitutively expressing either a beta-galactosidase gene or a different type of luciferase gene. To obtain luciferase expression, recombinant cells were grown for about 24–48 hours after transfection in standard media. Luciferase activity in the recombinant cells was then determined by lysing the cells, by taking the supernatant after centrifugation, and by adding 100 microliters of luciferase substrate to 20 microliters of supernatant followed by an immediate measurement of light emission using a Turner Design 20/20 luminometer (available from VWR, Bridgeport, N.J.).

The experiments were repeated at least three times in each of the different cell lines and the results of three independent experiments are shown in FIG. 1. The results indicate that use of the CYP4502A6 promoter region containing the polymorphic site produced about a 3- to 5-fold less luciferase activity compared to use of the promoter from the wildtype allele.

Example 4

This example describes the association of the Promoter −39 CYP4502A6 polymorphism described in Example 1 with the occurrence of asthma.

Genomic DNA was isolated from blood lymphocytes of 223 individuals with asthma and 256 individuals without asthma using standard methods. Taqman assays were performed using DNA samples from each individual to identify the presence or absence of the Promoter −39 CYP4502A6 variant (SEQ ID NO:18). The following primers were used:

| PCR Primer | SEQ ID NO: | Primer Sequence |
|---|---|---|
| 2A6-39 for | 26 | TGGGAGGTGAAATGAGGTAATTATG |
| 2A6-39 rev | 27 | GTACCACCATCTCCCTACTATCTAC |

PCR amplification was performed at a $Mg_2Cl$ concentration of 5 mM. Thermal cycling was performed with an initial denaturation step at 95° C. for 10 min, followed by 47 cycles of denaturation at 94° C. for 30 sec, primer annealing and extension at 62° C. for 60 sec. The resulting PCR products were resolved using standard gel electrophoresis methods and hybridized to the following probes: 5' TCAGGCAG-TATAAAGGCAAACCACCC 3' (wildtype, SEQ ID NO:28) and 5' TTCAGGCAGTAGAAAGGCAAACCACC 3' (mutant, SEQ ID NO:29). The resulting flourescence from the hybridization was measured using a fluorometer to determine the occurrence of the polymorphic sites and homo- or heterozygosity. The results are shown below in Table 5.

TABLE 5

CYP4502A6 Variants and Asthma. The chi-square p-value comparing the observed to expected in this Table is 0.01. The relative risk of asthma for those with asthma versus those without the variant (assuming a dominant model) is 0.53 (95% CI 0.30 0.93) with a corresponding p-value = 0.03. The A allele is wildtype and the B allele is mutant.

| Asthma | Alleles (Freq/%) | | | Total |
|---|---|---|---|---|
| | AA | AB | BB | |
| NO | 214 | 37 | 5 | 256 |
| | 83.59% | 14.45% | 1.95% | |
| YES | 202 | 21 | 0 | 223 |
| | 90.58% | 9.42% | 0% | |
| Total | 416 | 58 | 5 | 479 |

The results indicate that individuals have about a 2-fold decreased risk of developing asthma if they have the B allele than if they are homozygous for the A allele. Thus, the data suggests that the Promoter −39 variation has protective value against developing asthma. In addition, the data indicates that being homozygous for the A allele has little predictive value.

Example 5

This example describes the association of the Promoter −39 CYP4502A6 polymorphism described in Example 1 with the occurrence of smoking.

Results from the PCR reactions performed in Example 3 to identify the presence or absence of the Promoter −39 CYP4502A6 variant (SEQ ID NO:18) were correlated with smoker versus non-smoker information from each individual. The results are shown below in Table 6.

TABLE 6

CYP4502A6 Variants and Smoking.

| Smoking Status | Alleles | | | Total |
|---|---|---|---|---|
| | AA | AB | BB | |
| >1 pack/day | 36 | 3 | 0 | 39 |
| | 92% | 8% | 0% | |
| >5 cigs-<1 pack/day | 138 | 18 | 1 | 157 |
| | 88% | 11.5% | 0.5% | |
| <5 cigs/day | 43 | 11 | 1 | 55 |
| | 78% | 20% | 2% | |

The results indicate that there is a trend toward increased cigarette consumption among those individuals without the variant at a statistical significance of p=0.1. There was no difference in variant status among those individuals who smoked compared with those who never smoked.

Example 6

This example is a comparison of the wildtype sequence for cytochrome P450 2A6 (CYP4502A6) reported in the literature and having GENEBANK® Accession No. U22027 with the wildtype sequence for cytochrome P450 2A6 (CYP4502A6) of the present invention and being Identified as SEQ ID NO:21.

A comparison of GENEBANK® Accession No. U22027 and SEQ ID NO:21 is shown below in Table 7.

TABLE 7

| Position as referenced by SEQ ID NO:21 | Difference | Nucleotide of SEQ ID NO:21 | GENBANK® Accession No. U22027 |
|---|---|---|---|
| 75 | substitution | C | G |
| 141 | insertion | A | — |
| 144 | substitution | A | T |
| between 198 and 199 | deletion | — | G |
| 423 | substitution | A | G |
| 78 | substitution | A | T |
| 828 | substitution | T | C |

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for evaluating an individual's risk of developing asthma, comprising:
   detecting the presence or absence in the individual of a G polymorphism at promoter position—39 of the CYP2A6 gene and
   making an evaluation that the individual has a lower risk of developing asthma if the G polymorphism is present in the individual than if the G polymorphism is absent.

2. A method for evaluating an individual's propensity for cigarette consumption, comprising:
   detecting the presence or absence in the individual of a G polymorphism at promoter position—39 of the CYP2A6 gene; and
   making an evaluation that the individual has a greater propensity for an elevated cigarette consumption if the polymorphic is absent in the individual than if the polymorphism is present.

3. The method of claim 1, wherein the evaluation is that the individual has about a 2-fold lower risk of developing asthma if the G polymorphism is present in the individual than if the G polymorphism is absent.

4. The method of claim 1, wherein said deleting comprises detecting whether the individual is homozygous or heterozygous for the G polymorphism.

5. The method of claim 2, wherein the elevated cigarette consumption is greater than 5 cigarettes/day.

6. The method of claim 2, wherein the elevated cigarette consumption is greater than a pack of cigarettes/day.

7. The method of claim 2, wherein said detecting comprises detecting whether the individual is homozygous or heterozygous for the G polymorphism.

8. A method for screening an individual for propensity for reduced metabolism of a CYP2A6 substrate, the method comprising:

detecting the presence or absence in the individual of a G polymorphism at promoter position—39 of the CYP2A6 gene; and identifying the individual as having a propensity for reduced metabolism of the CYP2A6 substrate if the G polymorphism is present in the individual.

9. The method of claim 8, wherein said detecting comprises detecting whether the individual is homozygous or heterozygous for the G polymorphism.

10. The method of claim 8, wherein the CYP2A6 substrate is nicotine.

* * * * *

SEQUENCE LISTING

```
<160> NUMBER OF SEQ ID NOS: 29

<210> SEQ ID NO 1
<211> LENGTH: 16
<212> TYPE: DNA
<213> ORGANISM: Homo sapiens

<400> SEQUENCE: 1
ttcccctgaa atatgg                                                    16

<210> SEQ ID NO 2
<211> LENGTH: 16
<212> TYPE: DNA
<213> ORGANISM: Homo sapiens

<400> SEQUENCE: 2
cttctccctg tcttgg                                                    16

<210> SEQ ID NO 3
<211> LENGTH: 16
<212> TYPE: DNA
<213> ORGANISM: Homo sapiens

<400> SEQUENCE: 3
ttcccctgaa atatgg                                                    16

<210> SEQ ID NO 4
<211> LENGTH: 18
<212> TYPE: DNA
<213> ORGANISM: Homo sapiens

<400> SEQUENCE: 4
gccacacttt gtcttacc                                                  18

<210> SEQ ID NO 5
<211> LENGTH: 16
<212> TYPE: DNA
<213> ORGANISM: Homo sapiens

<400> SEQUENCE: 5
tggggcttgt agttgg                                                    16

<210> SEQ ID NO 6
<211> LENGTH: 16
<212> TYPE: DNA
<213> ORGANISM: Homo sapiens

<400> SEQUENCE: 6
ctgttgtgga ggatgc                                                    16

<210> SEQ ID NO 7
<211> LENGTH: 20
<212> TYPE: DNA
<213> ORGANISM: Homo sapiens

<400> SEQUENCE: 7
ggtctgtggt acttcaggag                                                20

<210> SEQ ID NO 8
<211> LENGTH: 16
<212> TYPE: DNA
<213> ORGANISM: Homo sapiens
```

-continued

```
<400> SEQUENCE: 8
caatgaaggg caatgg                                              16

<210> SEQ ID NO 9
<211> LENGTH: 15
<212> TYPE: DNA
<213> ORGANISM: Homo sapiens

<400> SEQUENCE: 9
gaacccgctg ggctt                                               15

<210> SEQ ID NO 10
<211> LENGTH: 15
<212> TYPE: DNA
<213> ORGANISM: Homo sapiens

<400> SEQUENCE: 10
gaacccgttg ggctt                                               15

<210> SEQ ID NO 11
<211> LENGTH: 17
<212> TYPE: DNA
<213> ORGANISM: Homo sapiens

<400> SEQUENCE: 11
actttgtctt accctaa                                             17

<210> SEQ ID NO 12
<211> LENGTH: 17
<212> TYPE: DNA
<213> ORGANISM: Homo sapiens

<400> SEQUENCE: 12
actttgtctc accctaa                                             17

<210> SEQ ID NO 13
<211> LENGTH: 17
<212> TYPE: DNA
<213> ORGANISM: Homo sapiens

<400> SEQUENCE: 13
gacctttgga ttcctct                                             17

<210> SEQ ID NO 14
<211> LENGTH: 17
<212> TYPE: DNA
<213> ORGANISM: Homo sapiens

<400> SEQUENCE: 14
gacctttgaa ttcctct                                             17

<210> SEQ ID NO 15
<211> LENGTH: 18
<212> TYPE: DNA
<213> ORGANISM: Homo sapiens

<400> SEQUENCE: 15
ccctggaacc cccagatc                                            18

<210> SEQ ID NO 16
<211> LENGTH: 18
<212> TYPE: DNA
```

-continued

```
<213> ORGANISM: Homo sapiens

<400> SEQUENCE: 16
ccctggaaca cccagatc                                                   18

<210> SEQ ID NO 17
<211> LENGTH: 18
<212> TYPE: DNA
<213> ORGANISM: Homo sapiens

<400> SEQUENCE: 17
caggcagtat aaaggcaa                                                   18

<210> SEQ ID NO 18
<211> LENGTH: 18
<212> TYPE: DNA
<213> ORGANISM: Homo sapiens

<400> SEQUENCE: 18
caggcagtag aaaggcaa                                                   18

<210> SEQ ID NO 19
<211> LENGTH: 17
<212> TYPE: DNA
<213> ORGANISM: Homo sapiens

<400> SEQUENCE: 19
cctgactgtg atggtct                                                    17

<210> SEQ ID NO 20
<211> LENGTH: 17
<212> TYPE: DNA
<213> ORGANISM: Homo sapiens

<400> SEQUENCE: 20
cctgactgta atggtct                                                    17

<210> SEQ ID NO 21
<211> LENGTH: 992
<212> TYPE: DNA
<213> ORGANISM: Homo sapiens

<400> SEQUENCE: 21
aagttcccct gaaatatggc tctggtcttc ctccccttgc caatgaagaa gatggcagtg     60
gaggttctat ggcacccatc ctggcctcac tctgaggttc aatgaggat tctgggcatc    120 aagagacagc tctgggcaaa agcaaaatca gtcagcccc tggacccagt gctgggctgc    180
tgggctttct gggagaaccc gctgggcttg ctacacactc ctcctcccag aaactccaca   240
cccacagccc tgggtcttcc tagccccgag actttcaagt ccatatgcct ggaatccccc   300
ttcctgagac ccttaaccct gcatcctcca aacagaaga cccctaaatg cacagccaca   360
ctttgtctta ccctaataaa acccagacct ttggattcct ctcccctgga acccccagat   420
ccacacaact ttggggtgca ttctcactct cagaccccaa atccaaagcc caagtgctcc   480
cctatgcaaa tattccaaac tcctcagttc tacagcttat ctgttgcccc ctcctaaatc   540
cacagccctg cggcacccct cctgaagtac cacagattta gtctggaggc cccctctctg   600
ttcagctgcc ctggggtccc cttatcctcc cttgctggct gtgtcccaag ctaggcagga   660
ttcatggtgg ggcatgtagt tgggaggtga atgaggtaa ttatgtaatc agccaaagtc   720
catccctctt tttcaggcag tataaaggca aaccacccca gccgtcacca tctatcatcc   780
```

```
cactaccacc atgctggcct cagggatgct tctggtggcc ttgctggtct gcctgactgt      840
gatggtcttg atgtctgttt ggcagcagag gaagagcaag gggaagctgc ctccgggacc      900 cacccccattg cccttcattg gaaactacct gcagctgaac acagagcaga tgtacaactc     960
cctcatgaag gtgtcccaag acagggagat gg                                    992
```

<210> SEQ ID NO 22
<211> LENGTH: 744
<212> TYPE: DNA
<213> ORGANISM: Homo sapiens

<400> SEQUENCE: 22

```
agaagatggc agtggaggtt ctatggcacc catcctggcc tcactctgag gttccaatga       60
ggattctggg catcaagaga cagctctggg caaaagcaaa atcaagtcag cccctggacc      120
cagtgctggg ctgctgggct ttctgggaga acccgctggg cttgctacac actcctcctc      180
ccagaaactc cacacccaca gccctgggtc ttcctagccc cgagactttc aagtccatat      240
gcctggaatc cccttcctg agacccttaa ccctgcatcc tccacaacag aagacccta       300 aatgcacagc cacactttgt cttaccctaa taaaacccag acctttggat tcctctcccc      360
tggaaccccc agatccacac aactttgggg tgcattctca ctctcagacc ccaaatccaa      420
agcccaagtg ctcccctatg caaatattcc aaactcctca gttctacagc ttatctgttg      480
ccccctccta aatccacagc cctgcggcac ccctcctgaa gtaccacaga tttagtctgg      540
aggccccctc tctgttcagc tgccctgggg tcccctttatc ctcccttgct ggctgtgtcc     600
caagctaggc aggattcatg gtggggcatg tagttgggag gtgaaatgag gtaattatgt      660
aatcagccaa agtccatccc tcttttttcag gcagtataaa ggcaaaccac cccagccgtc      720
accatctatc atcccactac cacc                                             744
```

<210> SEQ ID NO 23
<211> LENGTH: 22
<212> TYPE: DNA
<213> ORGANISM: Homo sapiens

<400> SEQUENCE: 23

```
aagcttagaa gatggcagtg ga                                               22
```

<210> SEQ ID NO 24
<211> LENGTH: 21
<212> TYPE: DNA
<213> ORGANISM: Homo sapiens

<400> SEQUENCE: 24

```
gagctcggtg gtagagggat g                                                21
```

<210> SEQ ID NO 25
<211> LENGTH: 744
<212> TYPE: DNA
<213> ORGANISM: Homo sapiens

<400> SEQUENCE: 25

```
agaagatggc agtggaggtt ctatggcacc catcctggcc tcactctgag gttccaatga       60
ggattctggg catcaagaga cagctctggg caaaagcaaa atcaagtcag cccctggacc      120
cagtgctggg ctgctgggct ttctgggaga acccgctggg cttgctacac actcctcctc      180
ccagaaactc cacacccaca gccctgggtc ttcctagccc cgagactttc aagtccatat      240
```

```
gcctggaatc cccCttcctg agacccttaa ccctgcatcc tccacaacag aagaccccta    300
aatgcacagc cacactttgt cttaccctaa taaaacccag acctttggat tcctctcccc    360
tggaaccccc agatccacac aactttgggg tgcattctca ctctcagacc ccaaatccaa    420
agcccaagtg ctccctatg caaatattcc aaactcctca gttctacagc ttatctgttg     480
ccccctccta aatccacagc cctgcggcac ccctcctgaa gtaccacaga tttagtctgg    540 aggcccctc tctgttcagc tgccctgggg tcccCttatc ctcccttgct ggctgtgtcc      600
caagctaggc aggattcatg gtggggcatg tagttgggag gtgaaatgag gtaattatgt    660
aatcagccaa agtccatccc tcttttcag gcagtagaaa ggcaaaccac cccagccgtc    720
accatctatc atcccactac cacc                                           744

<210> SEQ ID NO 26
<211> LENGTH: 25
<212> TYPE: DNA
<213> ORGANISM: Homo sapiens

<400> SEQUENCE: 26
tgggaggtga aatgaggtaa ttatg                                          25

<210> SEQ ID NO 27
<211> LENGTH: 25
<212> TYPE: DNA
<213> ORGANISM: Homo sapiens

<400> SEQUENCE: 27
gtaccaccat ctccctacta tctac                                          25

<210> SEQ ID NO 28
<211> LENGTH: 26
<212> TYPE: DNA
<213> ORGANISM: Homo sapiens

<400> SEQUENCE: 28
tcaggcagta taaaggcaaa ccaccc                                         26

<210> SEQ ID NO 29
<211> LENGTH: 26
<212> TYPE: DNA
<213> ORGANISM: Homo sapiens

<400> SEQUENCE: 29
ttcaggcagt agaaaggcaa accacc                                         26
```